United States Patent [19]

Faderl et al.

[11] Patent Number: 5,825,524

[45] Date of Patent: Oct. 20, 1998

[54] TRANSVERSE ELECTRIC MODE ELECTRO-OPTIC CELL FOR A MODULATOR AND PROCESS FOR PRODUCING SUCH A CELL

[75] Inventors: Ingo Faderl, Clermont-Ferrand; Serge Valette, Grenoble, both of France

[73] Assignee: Commissariat A l'Energie Atomique, Paris, France

[21] Appl. No.: 553,795

[22] Filed: Oct. 23, 1995

[30] Foreign Application Priority Data

Oct. 25, 1994 [FR] France .................. 94 12736

[51] Int. Cl.$^6$ .................................................. G02F 1/03
[52] U.S. Cl. ........................................... 359/245; 385/2
[58] Field of Search ............................. 359/245, 246, 359/254; 385/2

[56] References Cited

U.S. PATENT DOCUMENTS

| | | |
|---|---|---|
| 4,887,884 | 12/1989 | Hayden . |
| 4,896,930 | 1/1990 | Tsuchitani et al. . |
| 5,396,363 | 3/1995 | Valette .................. 359/248 |
| 5,548,668 | 8/1996 | Schaffner ............... 385/1 |

FOREIGN PATENT DOCUMENTS

| | | |
|---|---|---|
| 0522637 | 1/1993 | European Pat. Off. . |
| 3809182 | 9/1988 | Germany . |
| 4202039 | 7/1993 | Germany . |

OTHER PUBLICATIONS

"A New Electro–Optic Modulator Based On Nonlinear Polymers and Silicon Nitride Working In Transverse Electrical Configuration", Faderl, I. et al., LETI (CEA–Technologies Avancees), Nov. 1993, Int. Conf. Hybrid Materials, Bierville (F).

"A Fabrication Process For The Integration and Passivation Of An Electro–Optic Polymer in an Integrated Optics Circuit", Faderl, I. et al., LETI (CEA–Technologies Avancees), Jan. 1994, ICONO 1, Val Thorens (F).

"Polarization–Independent Integrated Electro–Optic Phase Modulator in Polymers", A. Brauer, et al., Fraunhofer–Institution for Applied Optics and Precision Mechanics, Conference SPIE 2042 Optics Quebec 93.

"20 GHz Electro–Optic Polymer Mach–Zehnder Modulator", D.G. Girton et al., Appl. Phys. Lett. 58, Apr. 1991, pp. 1730–1732.

"Travelling–Wave Polymeric Optical Intensity Modulator With More Than 40 GHz of 3dB Electrical Bandwidth", C.C. Teng, Appl. Phys. Lett. 60, Mar. 1992, pp. 1538–1540.

*Primary Examiner*—Mark Hellner
*Attorney, Agent, or Firm*—Pearne, Gordon, McCoy & Granger LLP

[57] ABSTRACT

The invention relates to an transverse electric mode electro-optic cell for a modulator, as well as to its production process.

The cell has on a substrate (4), an active region (10), and modulation control electrodes (16) on either side of the active region (10). According to the invention, the cell has confinement regions (14) of a material having a lower refractive index and lower resistivity than the material of the active region, the confinement regions being positioned on either side and against the active region (10) and between the control electrodes (16).

14 Claims, 5 Drawing Sheets

TRANSVERSE ELECTRIC MODE ELECTRO-OPTIC CELL FOR A MODULATOR AND PROCESS FOR PRODUCING SUCH A CELL

DESCRIPTION

1. Technical Field

The present invention relates to a transverse electric mode electro-optic cell and its production process. It more particularly relates to electro-optic cells with nonlinear polymer materials, nonlinear hybrid materials or liquid crystals. These cells are used in electro-optic modulators. A transverse electric mode electro-optic cell is an electro-optic cell able to function in an optimum manner in the so-called electric transverse electromagnetic field polarization (electric field perpendicular to the plane of incidence defined by the propagation direction and the perpendicular to the propagation plane. Thus, the invention has numerous applications in the field of the processing of signals, optical telecommunications or in the production of sensors, spectrum analyzers and interferometry devices. A particular application is e.g. the production of a Mach-Zehnder interferometer.

2. Prior Art

It is pointed out that an optical waveguide structure generally consists of a buffer layer, an active layer and an upper layer stacked on a substrate, the active layer having a refractive index higher than that of the buffer and upper layers.

The electro-optic effect makes it possible to modify, under the action of an electric field, the refractive index of a material and therefore bring about various functions such as the phase or intensity modulation of a light signal, or the polarization change of said signal. The electric field is applied to the active material by means of electrodes called "control electrodes" in the remainder of the text. Reference can be made in this connection e.g. to documents 1 and 2 given at the end of the present description.

In order to produce a cell for an electro-optic modulator, the active layer e.g. incorporates nonlinear polymers such as those marketed under the designations DR1-PMMA (marketed by IBM in the USA) or PU11 (marketed by Flamel Technology France).

For said polymers to have a second order effect, in the present case the refractive index modification, it is necessary for all the chromophores of these polymers to be oriented in the same direction. This direction is dependent on the location of the electrodes making it possible to apply the electric field and the operating mode. In order to have the highest electro-optic coefficient, a transverse magnetic mode operation (TM) implies that the control electrodes are positioned above and below the active layer and a transverse electric mode operation (TE) implies that the electrodes are located on two sides of the active layer. The orientation of the polymer with respect to the arrangement of the electrodes is e.g. described in document 3 appearing at the end of the description.

The polymers are oriented by heating them to their vitreous temperature and by simultaneously applying a strong electric field, called the "polarization field". The polymer is then cooled, whilst maintaining the field, which makes it possible to maintain the orientation when the polymer is cold.

In order to exploit the greatest nonlinearity of the polymer, it is necessary for the electric polarization field, the electric modulation field applied to the active layer and the electric field of the optical wave to be all directed in the same direction. This explains the electrode configuration differences for TE and TM operating modes.

By definition, the term guiding structure is understood to relate to all the layers permitting the confinement of light. In general, a guiding structure has a core intercalated between layers of materials with refractive indices below that of the core. In order to ensure a lateral confinement of the light in the structure, the core and/or the material layer positioned above the core can have at least a limited width part. The lateral confinement can also be obtained by etching a groove in the material layer located beneath the core, so that at least part of the material forming the core is deposited in said groove. In the case of an electro-optic modulator, the core of the structure, referred to hereinafter as the "optical guide" (because it ensures the propagation of light) comprises an active material. When this active material is a polymer, the lateral confinement can also be directly obtained by a local modification of the active material under the effect of an irradiation thereof by ultraviolet radiation. Reference can be made in this connection e.g. to documents, 1, 2 or 3 designated at the end of the description.

The known electro-optic cells operating in accordance with the transverse electric mode suffer from a certain number of disadvantages and limitations both with respect to their operation and their industrial production.

One of the limitations results from the very high control voltage necessary for obtaining the nonlinear electro-optic effect. This high voltage is in particular due to the considerable spacing of the control electrodes, which create an electric field in the active material. However, it should be noted in this connection that it is not possible to move the electrodes closer together as a result of the shape and the extent of the optical beam in the material and consequently it is impossible to reduce the control voltage.

Another problem is linked with the very high bias voltage, which is necessary for applying the electric field during the orientation operation of the active material, in the present case the polymer. As is stated in document 1, the bias voltage can destroy certain parts of the modulator unless special precautions are taken.

Another disadvantage of a large number of active materials and in particular nonlinear polymers is that of their very great fragility. Polymers having interesting efficiency levels with respect to their electro-optic properties are not generally usable in existing industrial production processes. For example, numerous nonlinear polymers have difficulties in withstanding ultraviolet radiation, so that they break their dye and consequently destroy the nonlinear effect. However, the use of ultraviolet rays is frequent in processes for the deposition and etching of silica.

The fragility or brittleness of the polymers also leads to a poor resistance thereof to heating. Thus, many polymers are not able to withstand heating to above 150° C. They are therefore unusable in the production of devices requiring higher temperatures, such as annealing operations.

Other component production operations are also incompatible with the use of polymers. Nonlinear polymers cannot be spread in film form on a substrate or on a structure having patterns or surface inhomogeneities of a significant extent, such as e.g. thick electrodes.

A supplementary disadvantage of a large number of nonlinear polymers is their hygroscopic nature. Following the preparation of the polymer layer, the latter must be polarized, as described hereinbefore, in order to permit an electro-optic effect. The water which consequently enters the polymer generally softens its structure and leads to the disappearance of the order induced by the polarization of the layer. Therefore the non-linear effect disappears as the polymer layer takes up water.

The object of the present invention is to propose an electro-optic modulator, as well as its production process, requiring a lower bias voltage and control voltage and not suffering from the disadvantages referred to hereinbefore. Another object is to propose a production process avoiding any deterioration to the active material and which is easy to perform.

DESCRIPTION OF THE INVENTION

For this purpose, the invention proposes a transverse electric mode electro-optic modulator having at least one optical guide with an active region of a nonlinear material having a refractive index which can be modified under the application of an electric field to the material, and control electrodes for the application of the electric field located on either side of the guide, characterized in that it also comprises regions made from a confinement material positioned respectively on either side of and against the active region and between the control electrodes, the confinement material having a refractive index below that of the material of the active region and an electrical resistivity below that of the material of the active region.

As a result of the invention and in particular the presence of regions made from confinement material with a low refractive index, the width of the mode in the waveguide is reduced, so that it is possible to move closer to one another the control electrodes without bringing about significant losses to the optical wave confined in the active material. For an electro-optic cell, the control voltage is directly proportional to the spacing between the electrodes, so that it is possible to reduce said voltage. The confinement regions make it possible to reduce the control voltage by typically 30 to 40%. As a result of the confinement regions, it is also possible to reduce the bias voltage of the active material and in particular the nonlinear polymer during its orientation. Thus, the confinement regions make it possible to limit the polarization field to the active region.

The electro-optic modulator according to the invention has a structure making it possible to comply with the double requirement of a good light confinement and a propagation thereof without significant losses, as well as an optimum electric field confinement within the volume occupied by the material of the active region.

The use of a confinement material with a refractive index, whose real part is lower than that of the material of the active region ensures the good confinement of light. Moreover, an index whereof the imaginary part is low makes it possible to limit the propagation losses to negligible values.

As the confinement material also has a lower resistivity than the active material, a good electric confinement is possible without greatly modifying the optical extinction coefficient. For information purposes only, the active material can have a resistivity of approximately $10^{13} \Omega.cm$ or higher.

It should be noted that, for improving the electric confinement, the simplest idea would be, for comparison purposes, the placing of the control electrodes in the immediate vicinity of the active region material. The generally metallic electrodes effectively have a very low resistivity of approximately $10^{-6} \Omega.cm$. However, the metallic material of the electrodes has a refractive index, whose imaginary part is very high and consequently there are prohibitive light propagation losses.

Advantageously the confinement material of the device according to the invention can be chosen with a resistivity e.g. between $10^5$ and $10^{10} \Omega.cm$.

In a practical application it is considered that a light absorption of approximately $10^{-10}$ cm to $10^{-4}$ $cm^{-1}$ is negligible.

According to an advantageous aspect of the invention, the material of the active region can be a nonlinear polymer.

According to another aspect of the invention, the cell can also have a covering or overlap layer of the active region made from a material with a refractive index lower than that of the material of the active region and having a low dielectric constant, i.e. in general terms below 4. The material of said layer is chosen for its optical and electrical characteristics. It must have a low refractive index and a low dielectric constant in order to avoid any breakdown during polarization, i.e. the orientation of the active material.

The material of said layer can e.g. be doped silica or a polymer in accordance with the trademark Teflon AF of Du Pont de Nemours. Teflon AF has an optical index n=1.29 and a dielectric constant $\epsilon$=1.87 to 1.93 for a frequency of approximately 10 GHz.

The electro-optic cell can also have a support substrate for the active region, electrodes and confinement material, which has an etched part partly containing the active region. The etching of the substrate then ensures with the confinement material, the lateral confinement of light in the structure.

According to a special embodiment of the invention, the optical guide also has a ribbon of a material with a refractive index higher than that of the material of the active region. The ribbon extends along the active region and contributes to the light guidance.

The invention also relates to a process for the production of a cell for a modulator, as described hereinbefore. This process essentially comprises the following operations:

- formation of a substrate made from an electrically insulating material and having an index below that of the material of the active layer,
- formation of the control electrodes on the substrate,
- formation of confinement material regions,
- formation of a "sacrificial" material layer and configuration of the layer in accordance with a pattern making it possible to fix the location and shape of the active region,
- formation of a covering layer on the sacrificial material layer,
- production of at least one opening in the covering layer extending to the sacrificial material layer,
- elimination of the sacrificial material layer in order to form a cavity corresponding to the active region and filling the cavity with a nonlinear material.

As a result of this production process, it is possible to treat the integrated circuit boards in accordance with conventional methods for the production of the cell up to the time where the active material is introduced into the cavity. The use of brittle nonlinear polymers is consequently no longer incompatible with the production of the structure of a modulator. It is e.g. possible to carry out RIE etching operations using reaction ions (reactive ion etching) using $CF_4$ gas, which emits an ultra-violet and blue radiation.

In the same way, a non-planar surface for the deposition of the nonlinear material, as a result of the invention, no longer constitutes an obstacle, because the latter is no longer spread with the whirler as in the prior art.

In particular, the pattern of the control electrodes and the locations for receiving the optical fibres connected to the modulator or to the cell can be designed as a function of their own requirements and not as a function of the nonlinear material. It should be noted in this connection that it is also possible to connect the optical fibres to the modulator prior to the filling of the cavity with the active material.

The active or nonlinear material is also no longer exposed to the effects of acids, bases or solvents. An active material having a good efficiency in its optical properties can consequently be retained without taking account of its possible brittleness or fragility.

The control electrodes are preferably produced prior to the filling of the cavity with the active material. According to different embodiments of the process, they can e.g. be produced directly following the formation of the substrate, either after the formation of the reduced electric resistance, confinement material regions, or after the elimination of the sacrificial material. Depressions can also be etched in the substrate to receive the control electrodes and/or the active material.

Other features and advantages of the invention can be gathered from the following description given in non-limitative manner with reference to the attached drawings.

DETAILED DESCRIPTION OF EMBODIMENTS

For reasons of simplification, identical references are used for the corresponding parts of the different drawings described hereinafter. Moreover, the different parts of the drawings are not shown to scale. Moreover, as an example of the active material that of nonlinear polymers will be used.

Figure 1:
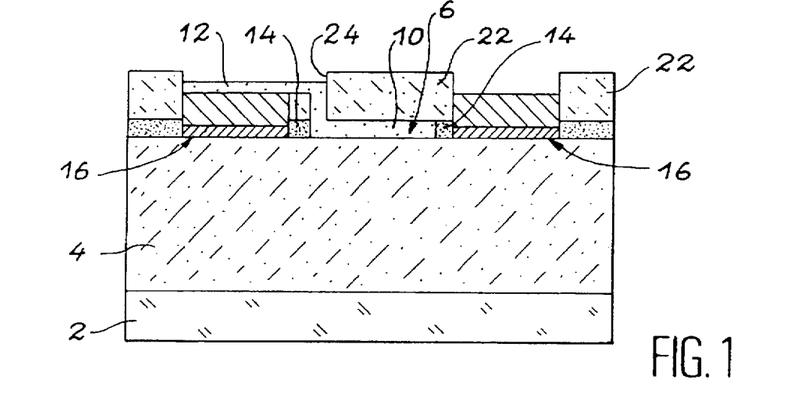
FIGS. 1 to 3 are diagrammatic sections of a modulator according to the invention.
Figure 2:
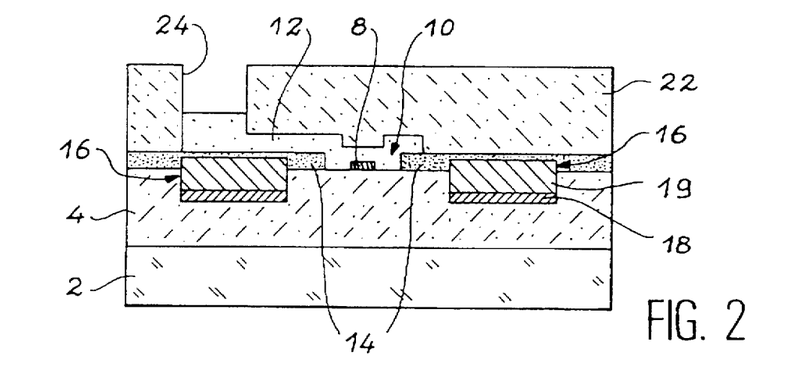
Figure 3:
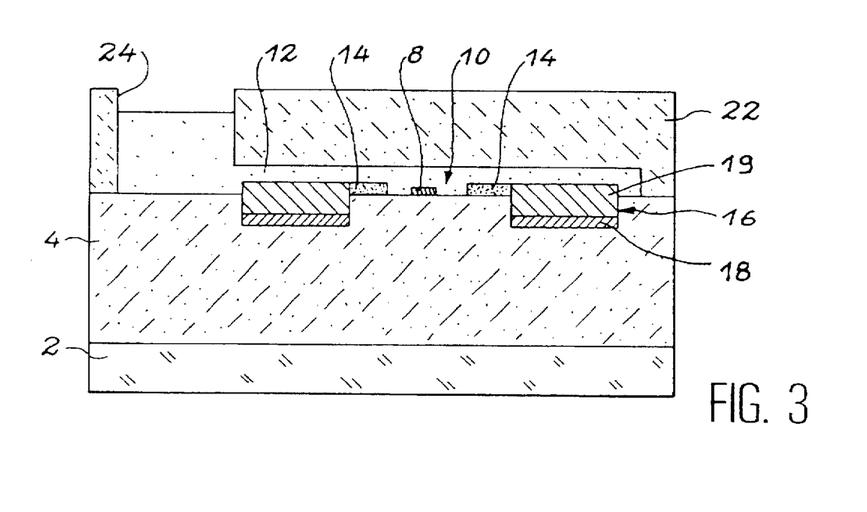

FIGS. 1 to 3 show the general structure of cells for modulators according to the invention. The cells have a silicon wafer 2 on which is formed a substrate 4, e.g. of phosphorus-doped silicon dioxide and having a thickness of approximately 10 μm.

A waveguide 6 has an active region 10 filled with an active material 12 such as a nonlinear polymer. According to the invention, the structure also has two regions 14 of a confinement material with an electric resistance below that of the active material. However, the material of the regions 14 remains an insulator, with a characteristic resistance lower by a factor of 10 to 100 than that of the active region. The regions 14 are e.g. made from highly nitrogen or phosphorus-doped silicon dioxide ($SiO_2$) in order to reduce the electric resistance thereof. They are in contact on either side and against the active material of the region 10. It is therefore possible to concentrate the electric field of the polarization in the active region during polymer orientation.

Control electrodes 16 are located on either side of the cavity and regions 14 and are in contact with the latter. The coplanar electrode 16 can be formed on the surface of the substrate 4, as shown in FIG. 1, but also in depressions etched in the substrate. This is the case with the modulators illustrated in FIGS. 2 and 3. As shown in the latter, the electrodes 16 can have a priming coating 18 on the substrate 4, essentially used for bringing about an electrolytic growth of a material 19, which forms the body of the electrode 16.

As shown in FIGS. 2 and 3, the waveguide 6 can also have a ribbon 8 of a material with a high refractive index, e.g. silicon nitride. The ribbon 8, which extends along the cavity, contributes to the lateral guidance of a light beam in the material.

A layer 22 covers the active region 10 and advantageously the regions 14. This layer can also cover the electrodes 16 (FIGS. 2 and 3). It can also be etched in order to subsequently form the electrodes 16, which in this case are not covered by the layer 22 (FIG. 1).

An opening 24 in the layer 22 permits the filling of the active region with a nonlinear polymer 12.

The figures show non-symmetrical structures, but it can be advantageous in certain operating modes, such as e.g. that of the push-pull type, to produce laterally symmetrical structures with respect to the optical guide.

The following table I gives in exemplified manner values relating to the dimensioning and materials of the different parts of the modulator.

TABLE I

| PART | DIMENSIONS | NATURE |
| --- | --- | --- |
| Wafer 2 | Thickness approx. 500 μm | Silicon |
| Substrate 4 | Thickness: 10 μm or more | Silicon dioxide ($SiO_2$) doped with 3% phosphorus (n = 1.468 at λ = 1.3 μm) |
| Material of regions 14 | Thickness: 0.5 to 2 μm, preferably 0.55 μm - width: variable | Silicon dioxide ($SiO_2$) doped with nitrogen or phosphorus, boron or fluorine (n = 1.5 at λ = 1.3 μm) |
| Ribbon 8 | Thickness: variable, preferably 0.09 μm - width: variable | Silicon nitride ($Si_3N_4$) (n = 1.979 at λ = 1.3 μm) |
| Electrodes 16 | Thickness: 50 to 20 μm width: 5 to 100 μm (e.g. 5 μm × 10 μm) electrode spacing: <20 μm and preferably 5 to 12 μm | Priming coating: chromium or titanium or aluminium Electrode body: Al, Au, Cu, Ag |

TABLE I-continued

| PART | DIMENSIONS | NATURE |
| --- | --- | --- |
| Covering layer 22 | Thickness: 1 to 10 µm | Doped silicon dioxide or polymer PMMA (n = 1.48) or Teflon AF (n = 1.29) |
| Active region 10 | Thickness: 0.5 to 1 µm - width 8 µm | Active polymer DR1-PMMA - PU11 (n ≡ 1.67) |

The term thickness in table I is understood in the direction of the stacking of the layers and the term width parallel to the surface of the substrate 4 in the sectional plane of the drawings.

Figure 4:
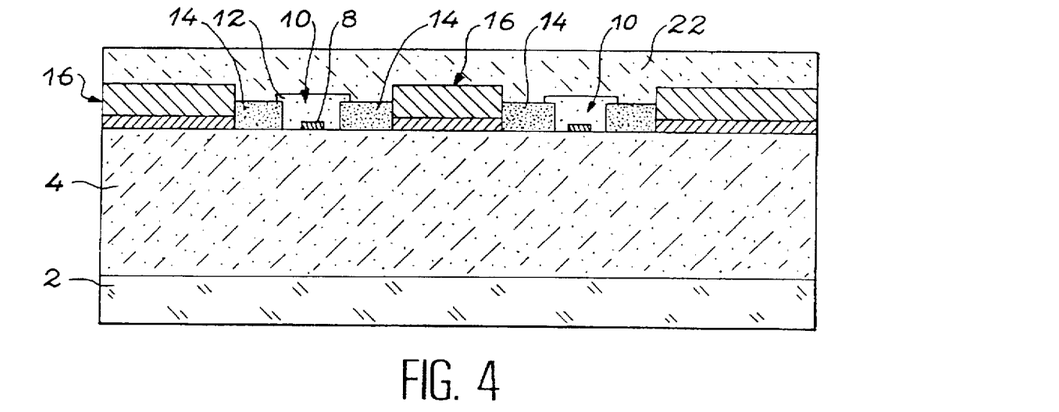
FIG. 4 is a diagrammatic section of a modulator according to the invention having two waveguides.

FIG. 4 shows a particular application of the invention where the cell is used in a Mach-Zehnder modulator. The cell comprises two coplanar waveguides 6 extending substantially parallel to one another. For further details on Mach-Zehnder interferometers, reference should be made to documents 2 and 4, 5 and 6 at the end of the present description.

FIG. 4 contains elements correspond to FIGS. 1 to 3, which carry identical references and for which reference should be made to the description concerning FIGS. 1 to 3. Whereas FIG. 4 can be understood as a section of a modulator having two active branches, each of FIGS. 1 to 3 can be considered as a section of a single branch of e.g. a Mach-Zehnder modulator.

It is pointed out that the modulator of FIG. 4 has a central electrode 16 common to the two waveguides 6. It should also be noted that the regions 10 can have a thickness slightly exceeding that of the regions 14. This characteristic gives the structure an improved wave confinement in the guides 6.

In general terms, several possibilities can be envisaged for defining the waveguide 6 of cells for modulators. FIGS. 5 to 8 illustrate in exemplified manner certain of these possibilities. For reasons of simplification, they only show the substrate 4, the active regions 10, the reduced electric resistance regions 14 and the covering layer 22, the electrodes 16 not being shown.

Figure 5:
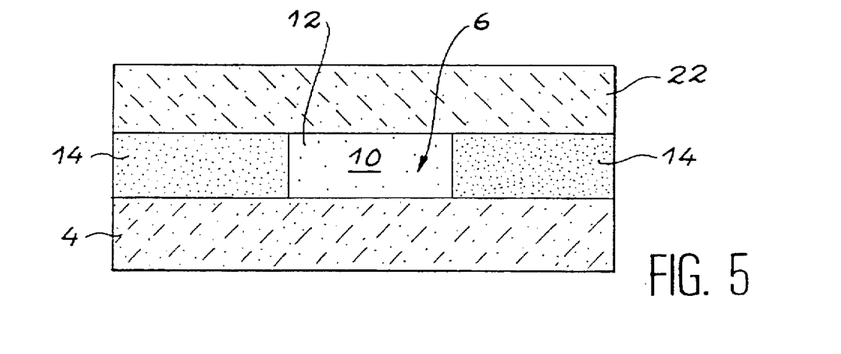
FIGS. 5 to 8 are diagrammatic sections illustrating constructional variants of the waveguide of a modulator according to the invention.

FIG. 5 shows a conventional guide, where the active polymer 12 is located between the two layers 4, 22, e.g. of silicon dioxide. The wave is guided in the polymer due to its index being higher than that of the surrounding materials 4, 14, 22.

Figure 6:
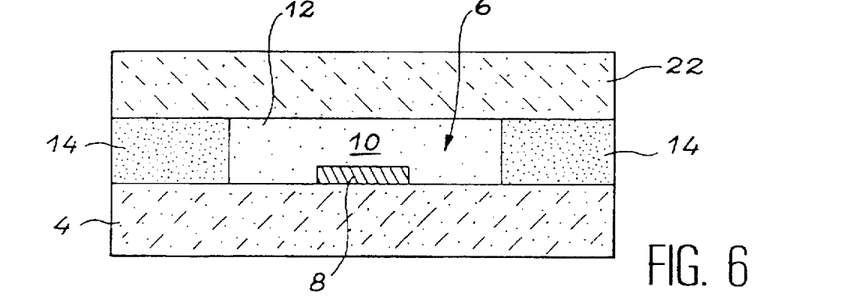

FIG. 6 shows a guide having a ribbon 8 extending along the active region and having a higher refractive index than that of the active polymer 12.

Figure 7:
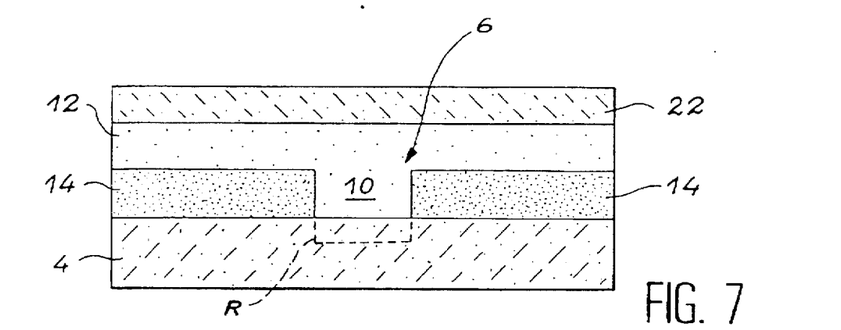

In FIG. 7, guidance is obtained by etching the reduced electric resistance material layer, which also permits the definition of the regions 14 and by the optional etching of a groove R in the substrate filled with the active material. In this case the active polymer is not solely located in the active region 10, but also extends above the regions 14.

Figure 8:
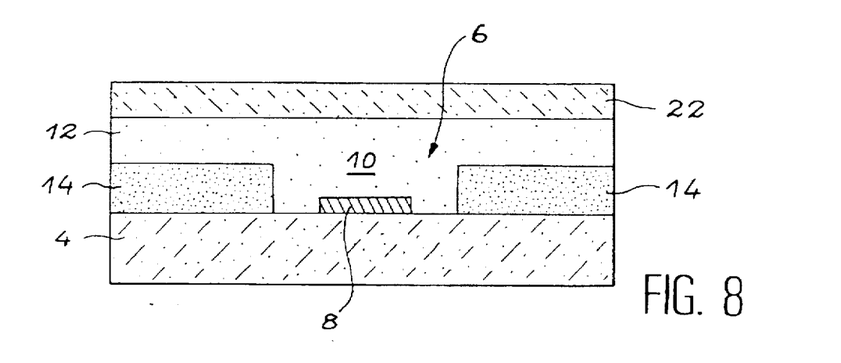

The guidance illustrated in FIG. 8 can be looked upon as a combination of the solutions of FIGS. 6 and 7. This results not only from the etching of the reduced resistance layer, but also the ribbon 8 formed in the active region 10. This is also the solution of FIGS. 2 and 3. In all the embodiments of FIGS. 5 to 8, a groove in the substrate can be used.

Figure 9:
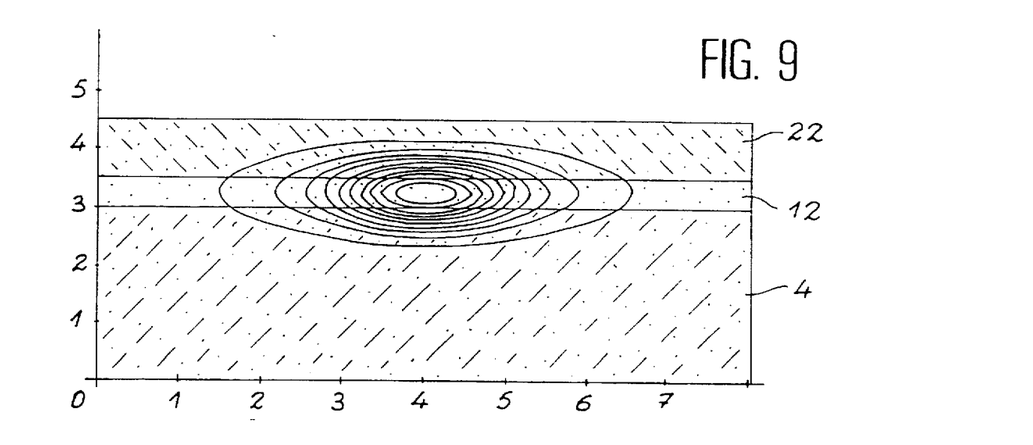
FIGS. 9 and 10 are diagrammatic sections respectively of the waveguide of a conventional modulator and a modulator according to the invention and illustrating the extension of the transverse electric mode.
Figure 10:
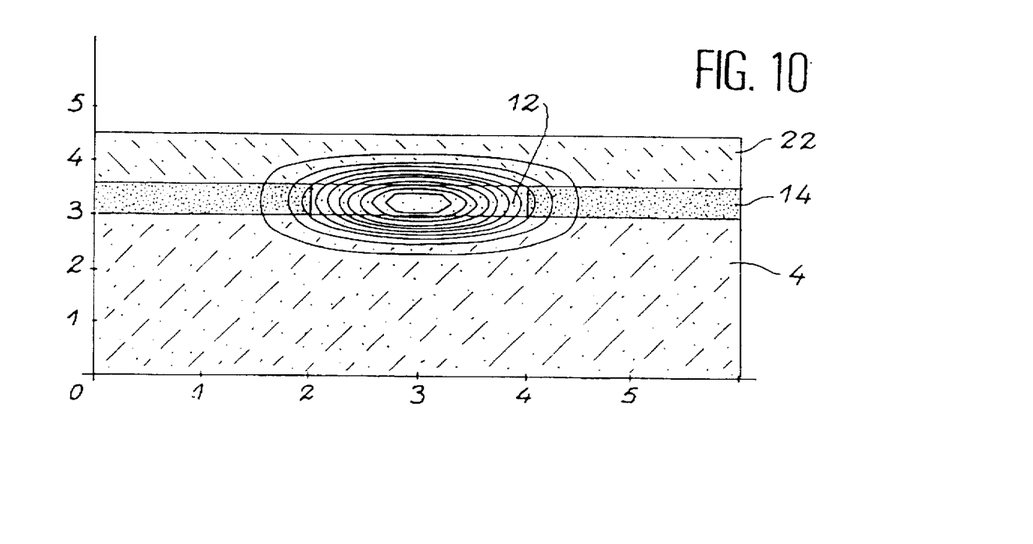

FIGS. 9 and 10 show the advantages obtained by the reduced resistance regions 14 in the electro-optic cells according to the invention. FIGS. 9 and 10 have abscissa and ordinate axes in µm to facilitate their reading.

In the case of FIG. 9, an active material layer 12 is located between the substrate 4 and a covering layer 22. However, there are no regions 14 for limiting the width of the optical mode. In the case of FIG. 10 a waveguide similar to that of FIG. 6 is obtained with the regions 14 having a reduced electrical resistivity according to the invention. The substrate 4 is a 3 µm thick silica layer with an index n=1.468. A not shown ribbon is also provided. It has a height of 0.9 µm, a width of 1.4 µm and an index n=1.979. The active polymer chosen is PU11 (n=1.685) with a thickness of 0.5 µm. The covering layer is a PMMA polymer (n=1.48). The total width of the guide defined between the material 14 is 2 µm. The control electrodes on either side of the material 14 are not shown so as not to overburden the drawings.

FIG. 10 shows that the width of the optical mode is reduced due to the regions 14 having a low index and reduced resistivity. On comparing the half-width of the modes of FIGS. 9 and 10, it can be seen that in FIG. 10, the half-width is reduced by approximately 40%. It is therefore possible to move together the not shown control electrodes by 10 to 6 µm without introducing any significant losses. Therefore the control voltage can be advantageously lowered by about 40%.

Figure 11:
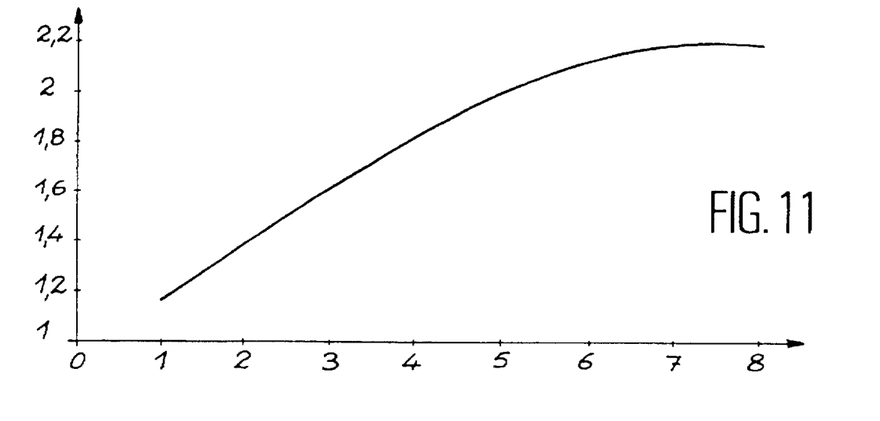
FIG. 11 is a curve showing for a modulator according to FIG. 10 the half-width of the TE mode as a function of the width of the active region of said modulator.

FIG. 11 is a curve showing for the cell of FIG. 10 the half-width of the TE mode, i.e. the electric component Ex of the electromagnetic field parallel to the substrate and perpendicular to the guide, as a function of the width of the active region. On the ordinate are given the values of Ex/10 in µm (corresponding to the half-width of the field Ex at −10 dB of the maximum value of the field) and on the abscissa the width of the active region in µm. The widths of the TE mode are measured at a location where the intensity of the mode is only equal to 1/100 of the intensity (corresponding to −20 dB) at the centre of the guide. In other words, the intensity decreases on moving away from the centre of the guide. FIG. 11 clearly shows that when the Width of the active polymer region decreases, the optical mode is more confined.

FIGS. 12 to 18 illustrate in exemplified manner an embodiment of the production process for a cell according to the invention.

Figure 12:
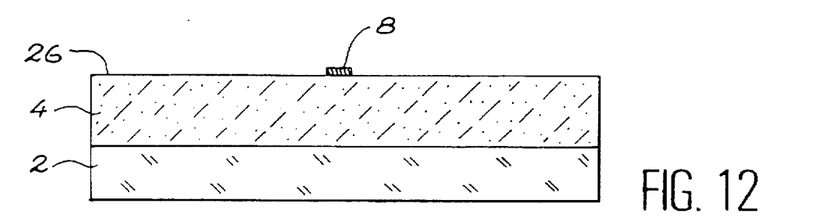
FIGS. 12 to 18 are diagrammatic sections illustrating the successive stages of a process for the production of the modulator according to the invention.
Figure 13:
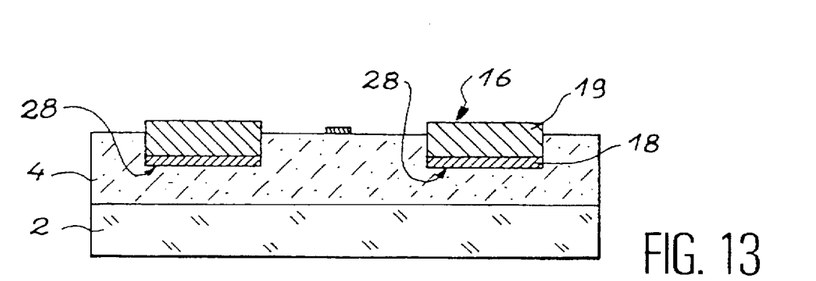

As is shown in FIG. 12, the production process firstly comprises the deposition of an e.g. silica layer 4 on a wafer 2. Following deposition, the surface 26 of the layer 4 is smoothed. A thin (0.09 µm) silicon nitride film is-deposited on the surface 26 and is then etched, e.g. by reactive ion etching so as to define the ribbon 8.

The process continues by the etching of depressions 28 in the surface 26 (FIG. 13) and the formation of control electrodes 16 in said depressions. The etching of the depressions can be a wet chemical etching (e.g. HF+HNF$_4$) or a dry etching by plasma of the RIE type e.g. using CHF$_3$ gas. The electrodes 16 are formed in two stages, a priming coating 18 is firstly formed in the depressions 28 and then a material 19 is formed by electrolysis on the layer 18.

After the formation of the electrodes 16, the complete structure can be made flat, but this operation is not illustrated in the drawings.

Figure 14:
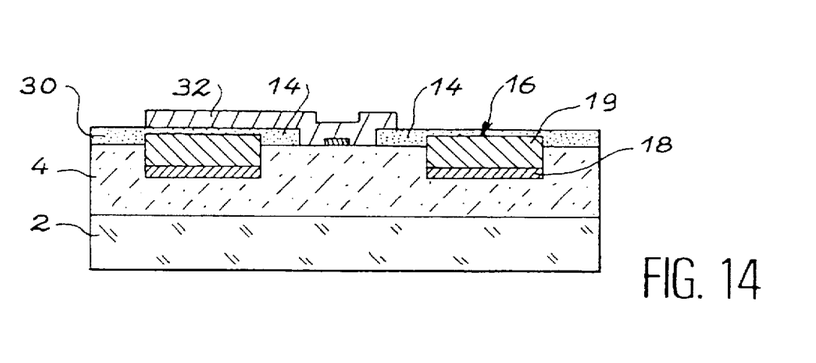
Figure 15:
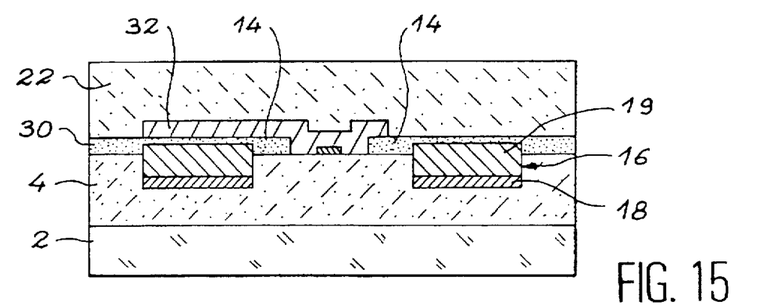

FIG. 14 illustrates the sequence of the process involving the deposition of a layer 30 of a material having a refractive index and resistivity below that of the active material. The layer 30, made from silica doped with nitrogen or phosphorus, or boron or fluorine, is etched so as to form the regions 14 according to the invention. A sacrificial material layer 32, e.g. of aluminium, is also deposited and then configured with a pattern making it possible to fix the shape and location not only of the active region, but more generally of the part containing the active material. The pattern can be obtained by etching or lift-off. The layers 30, 32 and the complete structure are then covered with an e.g. silica layer 22 (FIG. 15).

Figure 16:
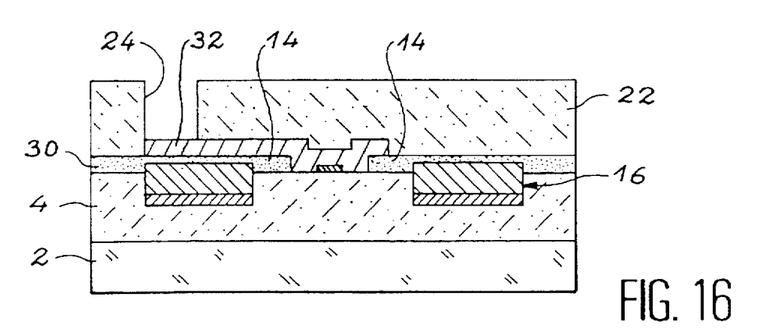
Figure 17:
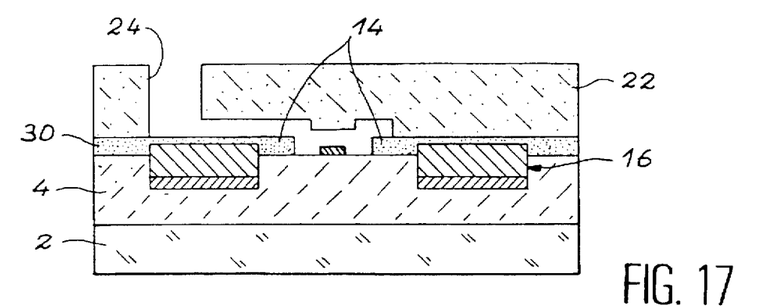
Figure 18:
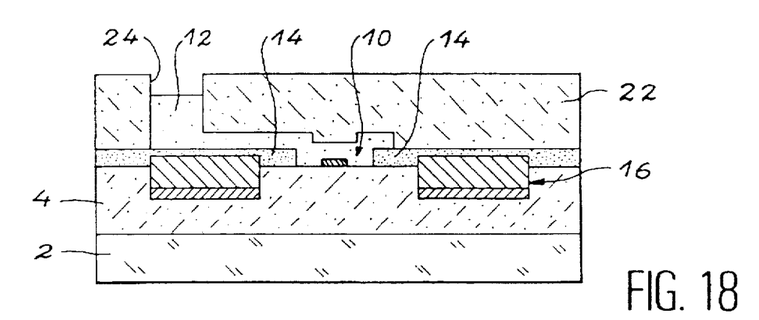

An opening 24, visible in FIG. 16, is then made in the layer 22. The opening 24 is etched down to the sacrificial material 32. A treatment with an appropriately chosen agent, in the present case sulphuric acid, makes it possible to eliminate the sacrificial material 32 and thus free a cavity having the pattern of the future active region. A rinsing with water and an annealing in a dry atmosphere also makes it possible to remove all substances remaining in the cavity. This cavity is shown in FIG. 17. As can be seen in FIG. 18, the cavity is finally filled with a nonlinear active polymer 12. The polymer is injected into the cavity, but a capillarity effect contributes to its correct filling. The injection of the polymer can take place in the presence of solvent vapour of the polymer in order to prevent a decomposition of the injected polymer and its solvent. An elongated shape of the cavity can help to give a preferred direction to the injected molecules. The cavity can be closed or open and its shape is adapted to the polymer or optionally the liquid crystal forming the active material.

A subsequent, not shown stage can consist of the passivation of the cell, e.g. with a n epoxy glue or an inert inorganic material, such as vapour-deposited silica.

According to variants of the process, the order of the different stages can be modified, e.g. the electrodes can be produced following the formation of the cavity, i.e. after eliminating the sacrificial material. However, it is preferable to perform all the operations liable to deteriorate the active material prior to the filling of the cavity therewith.

Finally, as a result of the invention, an easily produceable electro-optic cell is obtained, permitting the use of fragile or brittle, active materials and having the advantage of requiring a reduced modulator control voltage.

LIST OF DOCUMENTS REFERRED TO IN THE PRESENT APPLICATION (1) "A new electro-optic modulator based on nonlinear polymers and silicon nitride working in transverse electrical configuration", FADERL I., VALETTE S., GIDON P. REVOL F. LETI (CEA-Technologies Avancées) 08–11/11/93, Int. Conf. Hybrid Materials, Bierville (F).

(2) "A fabrication process for the integration and passivation of an electro-optic polymer in an integrated optics circuit" FADERL I. LABEYE P. GIDON P. MOTTIER P - LETI (CEA-Technologies Advancées) 09–13/01/94, ICONO 1, Val Thorens (F)

(3) "Polarization-independent integrated electro-optic phase modulator in polymers", A. BRAUER, T. GASE, L. ERDMANN, P DANNBERG, W. KARTHE Fraunhofer-Institution for Applied Optics and Precision Mechanics", Conference SPIE 2042 "Optics Quebec 93".

(4) "20 GHz electro-optic polymer Mach-Zehnder modulator" D. G. GIRTON, S. L. KWIATKOWSKI, G. F. LIPSCOMB and R. S. LYTEL, Appl. Phys. Lett. 58, 22 Apr. 1991, pp 1730–1732.

(5) U.S. Pat. No. 4,887,884

(6) "Travelling-wave polymeric optical intensity modulator with more than 40 GHz of 3 dB electrical bandwidth", C. C. TENG Appl. Phys. Lett. 60, 30 Mar. 1992, pp 1538–1540.

We claim:

1. Transverse electric mode electro-optic modulator having at least one optical guide (6) with an active region (10) of a nonlinear material (12) having a refractive index which can be modified under the application of an electric field to the material, and control electrodes (16) for the application of the electric field located on either side of the guide (6), characterized in that it also comprises regions (14) made from a confinement material positioned respectively on either side of and against the active region (10) and between the control electrodes (16), the confinement material having a refractive index below that of the material of the active region and an electrical resistivity below that of the material of the active region.

2. Electro-optic cell according to claim 1, characterized in that it has a covering layer (22) for the active region (10) made from a material with a refractive index below that of the material of the active region.

3. Electro-optic cell according to claim 2, characterized in that the material of the covering layer (22) is chosen from among doped silica and a polymer material.

4. Electro-optic cell according to claim 1, characterized in that the material (12) of the active region (10) is a nonlinear polymer.

5. Electro-optic cell according to claim 1, characterized in that the confinement material is silica doped with nitrogen or phosphorus, or boron or fluorine.

6. Electro-optic cell according to claim 1, characterized in that the optical guide (6) has a ribbon (8) of a material with a refractive index higher than that of the material (12) of the active region (10) and extending along the guide.

7. Electro-optic cell according to claim 1, characterized in that it has a support substrate for the active region, the electrodes and the confinement material, the substrate having an etched part partly containing the active region.

8. Process for the production of an electro-optic cell having at least one optical guide (6) with an active region (10) of a nonlinear material (12) having a refractive index which can be modified under the application of an electric field to the material, control electrodes (16) for the application of the electric field located on either side of the guide (6), and regions (14) made from a confinement material positioned respectively on either side of and against the active region (10) and between the control electrodes (16), the confinement material having a refractive index below that of the material of the active region and an electrical resistivity below that of the material of the active region, characterized in that it comprises the following operations:

- formation of a substrate (4) made from an electrically insulating material and having an index below that of the material of the active region,
- formation of the control electrodes (16) on the substrate (4),

- formation of confinement material regions (14).
- formation of a "sacrificial" material layer (32) and configuration of the layer in accordance with a pattern making it possible to fix the location and shape of the active region,
- formation of a covering layer (22) on the sacrificial material layer,
- production of at least one opening (24) in the covering layer extending to the sacrificial material layer (32).
- elimination of the sacrificial material layer (32) in order to form a cavity corresponding to the active region (10) and filling the cavity with a nonlinear material.

9. Process according to claim 8, characterized in that the control electrodes (16) are formed after the elimination of the sacrificial material (32).

10. Process according to claim 8, characterized in that the formation of the control electrodes (16) involves the deposition of a priming coating (18) at locations for the control electrodes and then a deposition of metal (19) on the priming coating by electrolytic growth.

11. Process according to claim 10, characterized in that the substrate is etched to form depressions (28) corresponding to the locations of the electrodes (16).

12. Process according to claim 8, characterized in that it also involves the formation on the substrate (4) of a ribbon (8) made from a material with a refractive index higher than that of the nonlinear material and extending longitudinally in the active region (10).

13. Electro-optic cell according to claim 1, characterized in that the confinement material has a resistivity between $10^5$ and $10^{10}$ $\Omega$cm.

14. Transverse electric mode Electro-optic modulator having at least one optical guide (6) with an active region (10) of a nonlinear material (12) having a refractive index which can be modified under the application of an electric field to the material, and control electrodes (16) for the application of the electric field located on either side of the guide (6), characterized in that it also comprises regions (14) made from a confinement material positioned respectively on either side of and against the active region (10) and between the control electrodes (16), the confinement material having a refractive index below that of the material of the active region and an electrical resistivity below that of the material of the active region; and a covering layer (22) for the active region (10) made from a material with a refractive index below that of the material of the active region.

* * * * *

UNITED STATES PATENT AND TRADEMARK OFFICE
CERTIFICATE OF CORRECTION

PATENT NO.   : 5,825,524
DATED        : October 20, 1998
INVENTOR(S)  : Faderl et al.

It is certified that error appears in the above-identified patent and that said Letters Patent is hereby corrected as shown below:

Column 4, Line 5, delete "$10^{-10}$ cm" and insert --$10^{-10}$ cm$^{-1}$--.

Column 7-8 (in table), Last Line, delete " $\cong$ " and insert -- $\simeq$ --.

Column 8, Lines 37-38, delete "-10 dB" and insert ---10dB--.

Column 8, Line 42, delete "-20 dB" and insert ---20dB--.

Column 8, Line 44, delete "Width" and insert --width--.

Column 9, Line 36, delete "a n" and insert --an--.

Column 10, Line 9, delete "3 dB" and insert --3dB--.

Signed and Sealed this

Thirtieth Day of March, 1999

Attest:

Attesting Officer

Q. TODD DICKINSON

Acting Commissioner of Patents and Trademarks